United States Patent [19]

Parks, Jr. et al.

[11] Patent Number: 5,006,325

[45] Date of Patent: Apr. 9, 1991

[54] PROCESS FOR THE RECOVERY OF NITRIC ACID

[75] Inventors: David L. Parks, Jr.; Carl J. Martin, both of Houston, Tex.

[73] Assignee: Air Products and Chemical, Inc., Allentown, Pa.

[21] Appl. No.: 399,654

[22] Filed: Aug. 28, 1989

[51] Int. Cl.$^5$ .................... C01B 21/46; C07C 79/10
[52] U.S. Cl. .................... 423/390; 568/932; 568/939; 568/940
[58] Field of Search ............... 568/927, 932, 934, 939, 568/940; 423/390

[56] References Cited

U.S. PATENT DOCUMENTS

| | | | |
|---|---|---|---|
| 1,793,304 | 2/1931 | Boyer | 568/939 |
| 2,739,174 | 3/1956 | Ross | 568/940 |
| 2,849,497 | 8/1958 | Buchanan | 260/645 |
| 3,780,116 | 12/1973 | Sahgal | 568/939 |
| 3,928,475 | 12/1975 | Dassel | 568/939 |
| 4,021,498 | 5/1977 | Alexanderson et al. | 260/645 |
| 4,257,986 | 3/1981 | Milligan et al. | 568/934 |
| 4,261,908 | 4/1981 | Schroeder et al. | 568/934 |
| 4,496,782 | 1/1985 | Carr | 568/934 |
| 4,642,396 | 2/1987 | Carr et al. | 568/934 |
| 4,650,912 | 3/1987 | Pohl et al. | 568/934 |

FOREIGN PATENT DOCUMENTS 1129466 5/1962 Fed. Rep. of Germany ...... 568/939
2338479.4 2/1975 Fed. Rep. of Germany .
17849 1/1988 Japan ................... 568/938

*Primary Examiner*—Wayne A. Langel

[57] ABSTRACT

This invention relates to an improved process for the recovery and regeneration of nitric acid from spent acid obtained from the mixed acid nitration of aromatic compounds. In that process a mixed acid of sulfuric acid and nitric acid is contacted with an aromatic composition at a temperature and pressure sufficient for producing a nitroaromatic composition and a spent acid containing unreacted nitric acid, sulfuric acid and solubilized nitroaromatic compounds in said spent acid. The improvement comprises initially heating the spent acid to a temperature of from about 120° to 200° C. for a time sufficient to convert said nitroaromatics in said spent acid to a nitroaromatic composition having a boiling point greater than 300° C. at atmospheric pressure and then flash distilling the hot spent acid containing nitroaromatics compositions at a pressure from about 5 to 15 psia and temperature of 150° to 200° C. Nitric acid is removed as an overhead vapor fraction in preselected concentration and sulfuric acid and nitroaromatics are obtained as a bottoms liquid stream from said flash distilling step. The nitroaromatics are then removed from the liquid stream. Sulfuric acid obtained from this process is essentially free of color and suited for concentration.

7 Claims, 1 Drawing Sheet

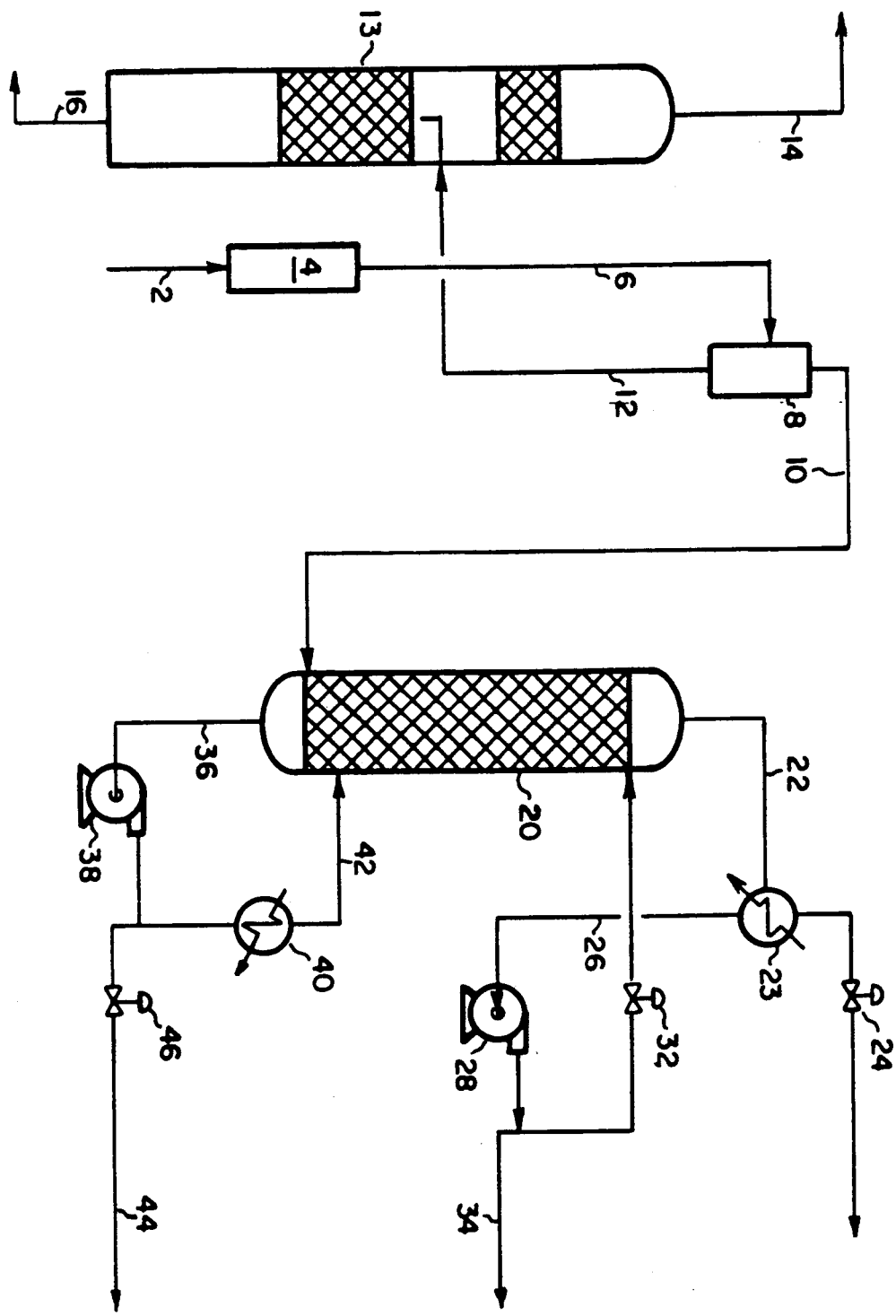

PROCESS FOR THE RECOVERY OF NITRIC ACID

TECHNICAL FIELD

This invention relates to an improved process for the recovery and concentration of nitric acid generated in the mixed acid nitration of aromatic compositions such as benzene and toluene.

BACKGROUND OF THE INVENTION

Nitration of aromatic compounds such as benzene and toluene to produce nitroaromatic compositions such as mononitrobenzene, dinitrobenzene, mononitrotoluene, dinitrotoluene, and trinitrotoluene has been carried out for a substantial period of time. Two techniques are primarily used on a commercial basis to produce mono and dinitrobenzene and nitrotoluenes. One nitration process involves the utilization of concentrated nitric acid, e.g., 95–98% nitric acid and the other involves the use of a mixed acid which comprises a mixture of sulfuric acid and nitric acid with the nitric acid concentration being about 63% to 67% and the sulfuric acid concentration being about 93% to 99% by weight. Both of the nitration processes generate a spent acid containing unreacted nitric acid, byproduct water and other impurities which must be removed from the product.

Various problems are associated with the recovery and concentration of nitric acid from spent acid by either nitration process, but recovery of nitric acid from spent acid generated in the mixed acid process and subsequent concentration of nitric acid and sulfuric acid for the nitration process, presents considerable problems. Several processes have been devised to recover nitric acid from this spent acid medium. Examples include:

U.S. Pat. No. 4,496,782 which discloses a process for denitrifying aqueous spent acid from the mononitration of aromatic compounds, e.g., toluene. As noted in that patent, the recovery of the nitric acid from the spent mixed acid should be done with a minimum of processing to avoid risk of discoloration (charring) of the sulfuric acid, as the charred or black spent acid is unacceptable in the industry. One of the techniques for recovering the nitric acid from the spent acid, has been to carry out the reaction with an excess of aromatic nitratable compound. Reference was made to U.S. Pat. No. 4,021,498 and 2,849,497 which shows contacting a crude nitrobenzene product containing nitric acid with fresh benzene.

U.S. Pat. No. 4,650,912 discloses a process for denitrifying nitric acid and nitrous acid-containing spent acid obtained from the nitration of aromatic hydrocarbons by adding aromatic hydrocarbon to the spent acid phase and photometrically monitoring the denitrification reaction for the appearance of a dark red to black color. At that point the aromatic hydrocarbon-nitric acid molar ratio was adjusted to eliminate color by reducing aromatic hydrocarbon feed rate or adding nitric acid to the medium.

German publication P23 38 479.4 discloses a process for the workup of nitric acid containing nitration products obtained by the nitration of aromatic compounds by using the concentrated nitric acid process. Because of the problems associated with the recovery of nitric acid from a solution of an organic nitrocompounds and concentrated nitric acid, sulfuric acid was added to the nitric acid-nitro aromatic solution and then the nitric acid recovered by distillation.

SUMMARY OF THE INVENTION

This invention pertains to an improved process for the recovery and concentration of nitric acid from a spent acid generated in the mixed sulfuric acid-nitric acid process for the nitration of aromatic compounds. More particularly, the improvement for recovering and concentrating nitric acid from a spent acid stream containing nitric acid, sulfuric acid and low boiling nitroaromatic compounds obtained from the nitration of an aromatic hydrocarbon by the mixed acid process comprises:

heating the spent acid stream containing sulfuric acid, nitric acid, and nitroaromatic compounds to a temperature of from about 120° to 200° C. for a time sufficient to convert low boiling nitroaromatic compounds having a boiling point of about 200° C. or less at atmospheric pressure to higher boiling nitroaromatic compounds having a boiling point of greater than 300° C. at atmospheric pressure; passing the heated sulfuric acid/nitric acid stream to a flash drum operated at a pressure ranging from 5 to 15 psia, thereby liberating nitric acid as an overhead and a sulfuric acid stream containing high boiling nitroaromatic compounds as a bottom liquid stream. The nitric acid vapor stream from the flash drum is cooled and then the resultant nitric acid stream is distilled to obtain a concentrated nitric acid bottoms and a water fraction as an overhead. In a preferred embodiment, the sulfuric acid recovered from the flash drum is charged to a stripping column wherein the nitroaromatic compounds are removed.

Significant advantages result from the practice of this invention and these advantages include:

an ability to recover and concentrate nitric acid from a spent acid obtained from the mixed acid nitration of aromatic compounds without charring or contaminating the sulfuric acid in the spent acid;

an ability to recover nitric acid from a stripping operation which reduces nitric acid in the wastewater streams., e.g., by producing a waste stream having reduced pH;

an ability to recover nitric acid in sufficient concentration for reuse in the mixed acid nitration of aromatic compounds; and an ability to recover sulfuric acid from the spent acid for reuse.

IN THE DRAWING

The drawing is a flow diagram of a process scheme for the recovery of nitric acid.

DETAILED DESCRIPTION OF THE INVENTION

To facilitate an understanding of the invention, reference is made to the drawing.

In the process, a spent acid obtained from the mixed acid nitration of aromatic compounds, e.g., benzene or toluene containing from 0.1 to 5% nitric acid, 65 to 75% sulfuric acid, and typically not more than about 2% by weight of nitroaromatic compounds having a boiling point of about 200° C. or less at atmospheric pressure is charged through line 2 to heat exchanger 4, wherein the spent acid phase is heated to a temperature ranging from about 120° to 200° C. During this heating stage, the nitroaromatic compounds having a boiling point of about 200° C. or less are converted to higher molecular weight nitroaromatic compounds which have a boiling point greater than about 300° C. at atmospheric pressure. Usually a residence time of less than one minute is required for this conversion step, but longer reaction time can be utilized without significant disadvantages.

Hot spent acid containing higher molecular weight nitroaromatic compounds are removed from heat exchanger 4 through line 6 and because of the greater relative volatility difference between the sulfuric acid and nitroaromatic compositions vis-a-vis nitric acid, nitric acid can be flashed. This is accomplished by passing the stream to flash drum 8 or other zone of reduced pressure which operates at a pressure typically ranging from about 5 to 15 psia and removing nitric acid as an overhead stream 10. As the flash drum operating temperature increases, more water is carried over with the vapor removed via line 10, thus effecting dilution of nitric acid vapor carried from flash drum 8. If the pressure in flash drum 8 is lowered, more water will also be carried over with the nitric acid.

A sulfuric acid/nitroaromatic compound water-containing stream is removed as a bottom liquid stream from flash drum 8 via line 12. The residual nitroaromatics in the stream are removed from that stream typically by charging the stream to steam stripping column 13 which is packed with various packings, e.g. Pall rings. Rashig rings, saddles or other packing. The nitroaromatic compounds are removed as an overhead via line 14 and sulfuric acid as a bottoms fraction via line 16. Unlike many of the prior extraction processes, the sulfuric acid removed from steam stripping column 13 is clear and is suitable for concentration in accordance with sulfuric acid concentration processes as described in U.S. Pat. No. 4,409,064 which is incorporated by reference.

Nitric acid from the flash drum is withdrawn as an overhead vapor through line 10 and then charged to distillation column 20. Distillation is carried out at a pressure of from about 2 psia to atmospheric pressure and at temperatures ranging from 50° to 200° C. An overhead is removed from column 20 through line 22 which is essentially free of nitric acid and a portion condensed in condenser 23. A portion of the vapor from condenser 23 is withdrawn through line 24 and liquid condensate withdrawn through line 26. A portion of the condensate is pumped via pump 28 for return to column 20 via line 30. Valve 32 is used to control the flowrate of condensate to the column as a reflux. Wastewater is discharged through line 34 to a sewer or disposal facility, if required.

A bottoms fraction of concentrated nitric acid is withdrawn from column 20 via line 36 by pump 38. The bottoms fraction contains nitric acid in a concentration range of from 45° to 65% by weight, which can be used as make-up for the mixed acid nitration of any aromatic composition such as benzene and toluene. A portion of the bottoms fraction is returned to the bottom of the column after heating in exchanger 40 via line 42 and the balance of the bottoms fraction withdrawn via line 44, the flow rate being controlled by valve 46.

The following example is provided to illustrate an embodiment of the invention is not intended to restrict the scope thereof.

EXAMPLE 1

A spent acid feed was processed in accordance with the flowscheme set forth in the drawing and the table below sets forth the process conditions, e.g.. flow rate, temperature, and pressure and approximate weight percent of the compounds at various stages within the process. Stream Numbers correspond to numbers in the drawing.

| Stream No. | NITRIC ACID RECOVERY MATERIAL BALANCE | | | | | | | | | |
|---|---|---|---|---|---|---|---|---|---|---|
| | 2 | 6 | 10 | 12 | 18 | 22 | 30 | 34 | 36 | 44 |
| FLOW, LB/HR | 100 | 100 | 95 | 5 | 20 | 15 | 21 | 6 | 15 | 5 |
| TEMP., °C. | 82 | 185 | 153 | 153 | 153 | 83 | 57 | 54 | 54 | 77 |
| PRESS., PSIA | 40 | 15.4 | 5.0 | 5.0 | 5.0 | 3.9 | 3.0 | 30 | 30 | 50 |
| Wt % Components | | | | | | | | | | |
| $H_2SO_4$ | 72 | 72 | — | 75.6 | — | — | — | — | 0.1 | 0.1 |
| $H_2O$ | 25.7 | 25.7 | 76.0 | 23.2 | 76.0 | 93.3 | 93.3 | 93.3 | 23.6 | 23.6 |
| $HNO_3$ | 1.0 | 0.9 | 16.3 | 0.1 | 16.3 | 0.1 | 0.1 | 0.1 | 64.9 | 64.9 |
| $HNO_2$ | 0.3 | 0.3 | 4.9 | 0.1 | 4.9 | 4.4 | 4.4 | 4.4 | 6.7 | 6.7 |
| MNT | 0.3 | 0.1 | 1.7 | — | 1.7 | 2.2 | 2.2 | 2.2 | — | — |
| DNT | 0.1 | 0.4 | 1.1 | 0.4 | 1.1 | — | — | — | 4.7 | 4.7 |
| n-CRESOLS | 0.6 | 0.6 | 0 | 0.6 | — | — | — | — | — | — | n-cresols refers to nitrocresols.

What is claimed is:

1. In a process for the recovery and regeneration of nitric acid from a spent acid obtained from the mixed acid nitration of aromatic compounds, wherein a mixed acid of sulfuric acid and nitric acid is contacted with an aromatic composition at a temperature and pressure sufficient for producing a nitroaromatic composition and a spent acid containing unreacted nitric acid, sulfuric acid and solublized nitroaromatic compounds in said spent acid, the improvement which comprises:

heating the spent acid to a temperature of from about 120° to 200° C. for a time sufficient to convert nitroaromatics in said spent acid to a nitroaromatic composition having a boiling point greater than 300° C. at atmospheric pressure;

flash distilling the resultant hot spent acid containing nitroaromatics compositions having a boiling point greater than 300° C., and removing nitric acid as an overhead vapor fraction in preselected concentration and a bottom liquid stream containing sulfuric acid and nitroaromatics.

2. The process of claim 1 wherein said spent acid is heated to a temperature from 120° to 200° C. for less than one minute.

3. The process of claim 1 wherein the flash distilling step is carried out at a pressure from 5 to 15 psia and a temperature from 150° to 200° C.

4. The process of claim 3 wherein the nitric acid removed as an overhead from said flash distilling is further distilled at a pressure from 2 psia to atmospheric pressure and a temperature from 50° to 200° C., for producing nitric acid as a bottoms fraction having a concentration of from 45 to 65 percent by weight.

5. The process of claim 4 in said aromatic compound is toluene.

6. The process of claim 4 wherein said aromatic compound is benzene.

7. The process of claim 5 wherein the mixture of nitroaromatics and sulfuric acid is charged to a column and the nitroaromatics removed by passing steam through the mixture and removing nitroaromatics as an overhead from the column and sulfuric acid as a bottoms.

* * * * *